United States Patent [19]
Saito et al.

[11] 3,969,087
[45] July 13, 1976

[54] GELS OF NONPOLAR LIQUIDS WITH N-ACYL AMINO ACIDS AND DERIVATIVES THEREOF AS GELLING AGENTS

[75] Inventors: Tadaomi Saito; Yoshimasa Matsuzawa; Sadayoshi Ninagawa, all of Yokohama; Masao Honna, Kawasaki; Masahiko Takesada, Tokyo; Masahiro Takehara, Fujisawa, all of Japan

[73] Assignee: Ajinomoto Co., Ltd., Tokyo, Japan

[22] Filed: Feb. 12, 1975

[21] Appl. No.: 549,488

[30] Foreign Application Priority Data

Aug. 7, 1974 Japan.............................. 49-90633
Aug. 7, 1974 Japan.............................. 49-90634

[52] U.S. Cl................................. 44/7 C; 44/7 D; 252/316
[51] Int. Cl.².......................................... C10L 7/02
[58] Field of Search................ 44/7 C, 7 D; 252/316

[56] References Cited
UNITED STATES PATENTS

| | | | |
|---|---|---|---|
| 3,064,047 | 11/1962 | Miller................................ | 44/7 C X |
| 3,613,372 | 10/1971 | Lissant.............................. | 44/7 C X |
| 3,850,586 | 11/1974 | Iwama et al....................... | 44/7 C X |
| 3,873,688 | 3/1975 | Kalopissis et al. .............. | 252/316 X |

Primary Examiner—Edward A. Miller
Attorney, Agent, or Firm—Oblon, Fisher, Spivak, McClelland & Maier

[57] ABSTRACT

A wide variety of non-polar organic liquids are converted into gels by homogeneously admixing the non-polar organic liquids with a small amount of certain N-acyl amino acids or derivatives of N-acyl amino acids such as esters, amides and amine salts of the N-acyl amino acids.

30 Claims, No Drawings

GELS OF NONPOLAR LIQUIDS WITH N-ACYL AMINO ACIDS AND DERIVATIVES THEREOF AS GELLING AGENTS

BACKGROUND OF THE INVENTION

1. Field of the Invention

The present invention relates to the gellation or solidification of non-polar organic liquids, and to products obtained therefrom.

2. Description of the Prior Art

Non-polar organic liquids are used for various purposes in fuels, motor oils, paints, cosmetics, edible oils and the like.

In the practical use of non-polar organic liquids, it is often desirable to render them solid. If a container is damaged or broken open, the organic liquids stored therein flow out and spread over a wide area, and recovery of the spilled liquid is difficult. If the spilled organic liquids are inflammable, they burn once ignited. For example, fire and smoke inhalation cause many deaths in otherwise survivable aircraft accidents. The fires usually are caused when the highly volatile fuel spills from damaged tanks and splatters over a wide area. Fuel vaporizes and is easily ignited by hot engine parts or sparks from metal impact. On the contrary, when fuels are gelled, the degree of vaporization and the extent to which the fuel is scattered upon impact are decreased, and so the danger of rapidly spreading fire or explosion is substantially reduced. Thus, gelled fuels are a significant safety factor in jet aircraft. Also, gelled fuels may be handled like fluid liquids under certain stress. Moreover, gelling agents for organic liquids are useful for facilitating the removal or recovery of spilled non-polar organic liquids or other aggregates of non-polar organic liquids, and for preventing the leakage or spillage of such non-polar organic liquids from leaking tanks or holes.

A need continues to exist for methods of gelling non-polar organic liquids to avoid the many problems when such liquids are spilled.

SUMMARY OF THE INVENTION

Accordingly, one object of the present invention is to provide a method of gelling non-polar organic liquids with N-acylamino acids and derivatives thereof.

Another object of the present invention is to provide a method of gelling flammable non-polar organic liquids with an N-acylamino acid or derivative thereof to increase the safety factor when handling such liquids.

Briefly, these objects and other objects of the present invention as hereinafter will become more readily apparent can be attained by a process of homogeneously admixing a non-polar organic liquid with a small amount of an N-acylamino acid or derivative thereof, and allowing the mixed solution to stand so that the gel might form.

DESCRIPTION OF THE PREFERRED EMBODIMENTS

According to the present invention, gels may be prepared by homogeneously admixing non-polar organic liquids with effectively small proportions of at least one of an N-acylamino acid related compound having the general formula:

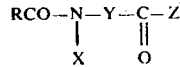   I.

wherein RCO is selected from the group consisting of $C_2$ to $C_{30}$ aliphatic acyl radicals and aralkyl acyl radicals, z is selected from the group of hydroxy, $-NH_2$, $-OR_1$, $-NHR_2$,

and $-O-R_5NH_3^+$ (where $R_1$, $R_2$, $R_3$, $R_4$, and $R_5$ are selected from $C_1$ to $C_{30}$ aliphatic hydrocarbon radicals and aralkyl radicals), X is hydrogen or methyl, and Y can be

(where $R_6$ is a $C_1$ to $C_4$ aliphatic hydrocarbon radical, benzyl, phenyl, $-CH_2OH$,

$-CH_2SH$, $-CH_2CH_2S-CH_3$, or $-(CH_2)_p-COZ$ (and $p$ is a positive integer of 1 or 2, and Z is the same as above), $-(CH_2)_m NHCOR$ (where $m$ is a positive integer of 3 or 4 and COR is the same as above) or $-(CH_2)_n-$ (where $n$ is a positive integer of 1 to 6), with the proviso that when Z is $-OR_1$,

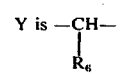

and $R_6$ is $-(CH_2)_m NHCOR$ and that at least one of R, $R_1$, $R_2$, $R_3$, $R_4$ or $R_5$ is a $C_5$ to $C_{30}$ aliphatic hydrocarbon radical to form a gel.

In the above general formula, the RCO radical is an aliphatic acyl radical derived from a saturated or unsaturated fatty acid having 2 to 30 carbon atoms such as, for example, acetic, acid, propionic acid, butyric acid, caproic acid, caprylic acid, capric acid, lauric acid, myristic acid, palmitic acid, stearic acid, oleic acid, linoleic acid, elaidic acid, 5 the naturally occurring mixed fatty acids, such as coconut oil fatty acid, tallow oil fatty acid or hydrogenated tallow oil fatty acid and synthetic fatty acids or an aralkyl acyl radical such as phenylacetyl, α-naphthaleneacetyl or hydrocinnamoyl. The $R_1$, $R_2$, $R_3$, $R_4$ and $R_5$ groups are $C_1$ to $C_{30}$ alkyl or alkenyl hydrocarbon radicals such as methyl, ethyl, propyl, butyl, amyl, hexyl, cyclohexyl, octyl, nonyl, decyl, dodecyl, undecylenyl, hendecyl, tridecyl, tetradecyl, cetyl, pentadecyl, heptadecyl, hexadecyl, hexadecenyl, octadecyl, octadecenyl, octadecadienyl, oleyl, elaidyl or mixtures thereof, or aralkyl radicals such as benzyl and hydrocinnamyl.

The amino acid moiety of the gelling agent having the above formula (I), i.e., the radical with the formula:

   II.

is preferably derived from acidic amino acids, neutral amino acids, sulfur containing amino acids, hydroxy amino acids, N-methyl derivatives of α-amino acids, ω-amides of acidic amino acids, basic amino acids, β-amino acids and ω-amino acids. Most preferably, the moiety expressed by formula (II) is derived from the group consisting of aspartic acid, glutamic acid, glutamine, glycine, sarcosine, α-alanine, β-alanine, α-aminobutyric acid, valine, norvaline, leucine, isoleucine, norleucine, phenylglycine, phenylalanine, serine, threonine, cysteine, methionine, $N^\delta$-acylornithine, $N^\epsilon$-acyllysine, γ-aminovaleric acid and ω-aminocaproic acid.

In the gelling agents of the present invention, at least one of the $C_5$ to $C_{30}$ higher aliphatic hydrocarbon radicals must be present either in the N-acyl moiety or in the other radical of the formula, i.e., the ester, amide or amine salt, or both moieties may contain a higher aliphatic hydrocarbon radical.

The following is a list of the number of gelling agents characterized by the above formula (I). The list of compounds is exemplary and presented for the purpose of illustration only and is not meant to be limiting in any manner.

1. Examples of the N-acyl amino acids include N-lauroyl-α-alanine, $N^\alpha$,$N^\delta$-dicaproyl-, $N^\alpha$,$N^\delta$-dicapryloyl-, $N^\alpha$,$N^\delta$-didecanonoyl-, $N^\alpha$,$N^\delta$-dilauroyl and $N^\alpha$,$N^\delta$-dicocoyl orithine (cocoyl means the acyl radical of coconut oil fatty acid), $N^\alpha$,$N^\epsilon$-dicaproyl-, $N^\alpha$,$N^\epsilon$-dicapryloyllysine, N-lauroyl valine and N-lauroyl glutamic acid.

2. Examples of the N-acyl amino acid esters include $N^\alpha$, $N^\delta$-dicaprylylornithine octyl, decyl, lauryl and stearyl esters, $N^\alpha$,$N^\epsilon$-dicapryloyllysine octyl, decyl and lauryl esters, $N^\alpha$,$N^\epsilon$-dilauroyllysine hexyl, octyl, decyl and lauryl esters, $N^\alpha$,$N^\epsilon$-dicocoyllysine hexyl, octyl, decyl and lauryl esters, $N^\alpha$,$N^\epsilon$-di(tallowyl) and $N^\alpha$,$N^\epsilon$-di(hydrogenated tallowyl) lysine hexyl, octyl, decyl and lauryl esters (tallowyl refers to the acyl radical of tallow oil fatty acid).

3. Examples of the N-acylamino acid amides include N-acetyl glutamic acid- α,γ-dilauryl and -α,γ-distearyl amides; N-caproyl glutamic acid-α,γ-diamide,α-γ, -dibutyl, -α,γ-dihexyl,-α,γ-dioctyl, -α,γ-dilauryl and -α,γ-distearyl amides; N-lauroyl glutamic acid -α,γ-diamide, -α,γ-dibutyl, -α,γ-dihexyl, -α,γ-dioctyl, -α,γ-dilauryl and -α,γ-distearyl amides; N-cocoyl glutamic acid -α,γ-diamide, -α,γ-dibutyl, -α,γ-dioctyl, -α,γ-dilauryl and -α,γ-distearyl amides; N-hydrogenated tallowyl glutamic acid -α,γ-diamide, -α,γ-dibutyl, -α,γ-dhexyl, -α,γ-dioctyl, -α,γ-dilauryl and -α,γ-distearyl amides; $N^\alpha$,$N^\epsilon$-diacetyllysine octyl, lauryl and stearyl amides; $N^\alpha$,$N^\epsilon$-dicaproyllysine amide butyl, hexyl, octyl, lauryl and stearyl amides; $N^\alpha$,$N^\epsilon$-dicaproyllysine amide, butyl, dibutyl, hexyl, octyl, lauryl and stearyl amides; $N^\alpha$,$N^\epsilon$-dilauroyllysine amide, butyl, dibutyl, hexyl, octyl, lauryl and stearyl amides; $N^\alpha$,$N^\epsilon$-dicocoyllysine amide, butyl, dibutyl, hexyl, octyl, lauryl, stearyl amides; $N^\alpha$,$N^\epsilon$-di(hydrogenated tallowyl) lysine amide, butyl, dibutyl, hexyl, octyl, lauryl and stearyl amides; N-lauroylvaline amide, butyl, hexyl, octyl and lauryl amides; N-lauroylphenylalanine amide, butyl, hexyl, octyl and lauryl amides; N-capryloyl leucine amide, butyl, hexyl, octyl and lauryl amides; and N-palmitoylmethionine amide, butyl, hexyl and octyl amides.

4. Examples of the N-acyl amino acid amine salts include $N^\alpha$,$N^\epsilon$-dicaproyllysine butyl, octyl, lauryl and stearyl amine salts; $N^\alpha$,$N^\epsilon$-dilauroyllysine butyl, octyl, lauryl and stearyl amine salts; $N^\alpha$,$N^\epsilon$-dicocoyllysine butyl, octyl, lauryl and stearyl amine salts; $N^\alpha$,$N^\epsilon$-di(hydrogenated tallowyl) lysine butyl, octyl, lauryl and stearyl amine salts; and N-lauroylphenylalanine octyl, lauryl, and stearyl amine salts.

The gelling agents which may be employed in this invention can agglomerate to form a coherent structure and trap the non-polar organic liquid within the gel matrix. On the other hand, the highly oil soluble derivatives of N-acyl amino acids such as N-acylglutamic acid diesters and N-acyl neutral amino acid esters cannot agglomerate to form a coherent structure and so cannot form a gel network.

Among the four kinds of gelling agents which may be employed in this invention, the N-acyl amino acids may be easily prepared by acylating the amino acid with acyl chloride in an aqueous media in the presence of a base such as sodium hydroxide. The ester or amide of the N-acylamino acid may be obtained by reacting an N-acyl amino acid with an alcohol or an amine (inclusive of ammonia) in the presence or absence of an acidic catalyst while heating. The amine salt of the N-acyl amino acid may be obtained by neutralizing the N-acyl amino acid with an amine.

The gels of this invention may be prepared simply by homogeneously admixing a gelling agent having the above formula (I) with non-polar organic liquids and then allowing the mixture to stand until gel formation occurs. Homogeneous mixture of the reactants may be conducted at temperatures ranging from room temperature to the boiling point of the non-polar organic liquid. The gelling agent may be added in the form of very fine powdered particles or as solutions dissolved in a suitable solvent such as acetone, methanol or ethanol, or in a small amount of the hot non-polar organic liquids to be gelled. The gel of the present invention may be formed by dissolving the gelling agent in a non-polar organic liquid at elevated temperatures, and thereafter cooling the resulting solution to a low temperature whereby gel formation occurs while standing. In all cases gel formation occurs as long as a mixture of a gelling agent and the non-polar organic liquid is sufficiently homogenized.

According to the present invention, the gelling agent may be employed generally in the range of 0.05% to 20% by weight based upon the amount of non-polar organic liquid to be gelled. The firmness of the resulting gel may be optionally varied depending on the kind and amount of gelling agent added. However, the addition of more than 10% by weight of the gelling agent causes no appreciable increase in the shear strength of the resultant gel. The preferred amount of the gelling agent is 0.1 to 10% by weight based upon the non-polar organic liquid. A suitable amount of gelling agent may be determined experimentally and it will vary with the desired physical properties of the gel and other components therein.

The non-polar organic liquids which can be gelled by the process of the present invention are generally almost any of those which have a dielectric constant of less than about 20 which have a solubility less than 10% by weight in water. Suitable examples of such non-polar organic liquids include petroleum hydrocarbons such as gasoline, naphthas, kerosine, gas oil, heavy oil and crude oil; lubricating oils such as spindle oil and turbine oil; liquid paraffin, pure hydrocarbons such as benzene, xylene, toluene, hexane, heptane, octane, and cyclohexane; esters such as butyl acetate, amyl acetate, diethyl phthalate, dibutyl phthalate, dioctyl phthalate, diethyl sebacate and dioctyl sebacate; ketones such as methyl isobutyl ketone and diisobutyl ketone; aldehyde such as anisaldehyde; chlorinated hydrocarbons such as carbon tetrachloride, tetrachloroethylene and chlorobenzene; phosphoric esters such as tributyl phosphate and tricresyl phosphate; normally liquid polyoxyalkylene monoalkyl ethers such as polyoxyethylenemonolauryl ether containing 4 to 6 oxyethylene units, polyoxypropylene mono $C_4$ to $C_{12}$ alkyl ether containing 10 to 50 oxypropylene units such as polyoxypropylene mono butyl ether, polyoxypropylene mono lauryl ether; normally liquid polyoxypropylene mono lauryl ether; normally liquid polyoxyalkylene glycol fatty acid esters, such as polyoxyethylene glycol lauric or oleic acid ester containing 4 to 6 oxyethylene units; fatty oils such as corn oil, soybean oil, olive oil, rape seed oil, cotton seed oil, sardine oil, herring oil and whale oil; silicone oil, mixtures thereof and liquids containing predominantly these non-polar organic liquids. On the other hand, organic liquids having a dielectric constant greater than about 20, such as acetone and ethanol, and having a solubility more than 10% by weight in water such as acetic acid and butyric acid do not gel satisfactorily.

The non-polar organic liquids may contain other ingredients as may be desired to achieve special effects. An emulsion or suspension of the non-polar organic liquid with water may be gelled. In the case of a system which forms a water in oil type emulsion or suspension wherein the water content is below 50%, the entire system may be gelled. And, in the case of a system which forms an oil in water type emulsion or suspension, the non-polar organic component may be gelled as an aggregate.

The gelling agent of the present invention is useful for the gelation of fuel oil and the recovery of drained oil. Furthermore, a wide variety of other materials can be prepared as for example, gelling or thixotropic agents for paints or inks, gelling agents for greases, solidifying agents for margarine comprising liquid oils, gelling agents or binders for liquid oil type cosmetics, binders or carriers for medicaments and gelling agents for napalm type incendiaries.

By the process of the present invention, gelled non-polar organic liquid are easily prepared with no involved procedures and the present gelling agents are capable of gelling non-polar organic liquid in only small amounts. Moreover, when the gelling agents of the present invention are employed for fuel oils, the fuels are gelled and the safety factor increases. Furthermore, the gelling agents themselves are flammable and they do not disturb the flammability of the fuel.

Having generally described the invention, a further understanding can be obtained by reference to certain specific examples which are provided herein for purposes of illustration only are not intended to be limiting unless otherwise specified.

EXAMPLE 1

One gram of each of the derivatives of N-acylamino acids shown in the table below was dissolved in 100 grams of kerosine with stirring at a temperature of 120°C. The resulting solutions were cooled to room temperature. After standing for 2 hours, gelled kerosine was prepared. Gelled olive oil was obtained similarly. The shear strength of these gels was measured with a rheo meter, RUD-J (a product of Fuji Rika Kogyo Co.). The results are tabulated below.

| Derivatives of N-acylamino acids | Shear strength of gel | |
|---|---|---|
| | Kerosine $g/cm^2$ | Olive Oil $g/cm^2$ |
| $N^\alpha, N^\epsilon$-dicaproyllysine lauryl ester | 36 | 122 |
| $N^\alpha, N^\epsilon$-distearoyllysine n-hexyl ester | 14 | 63 |
| $N^\alpha, N^\epsilon$-dilauroyllysine benzyl ester | 9.3 | 7.6 |
| $N^\alpha, N^\epsilon$-di(2-ethyl-hexanoyl)lysine lauryl ester | 15 | 16 |
| $N^\alpha, N^\epsilon$-dicaproyloylornithine lauryl ester | 13 | 36 |
| N-lauroylglutamic acid-$\alpha,\gamma$-diamide | 28 | 29 |
| N-lauroylglutamic acid-$\alpha,\gamma$-di-n-butylamide | 223 | 235 |
| N-lauroylglutamic acid-$\alpha,\gamma$-distearylamide | 41 | 26 |
| N-acetylglutamic acid-$\alpha,\gamma$-dilaurylamide | 13 | 25 |
| N-phenacetylglutamic acid-$\alpha,\gamma$-dilaurylamide | 11 | 10 |
| N-lauroylglutamic acid-$\alpha,\gamma$-di(2-ethyl hexylamide) | 35 | 28 |
| N-stearoyl aspartic acid-$\alpha,\beta$-di-n-butylamide | 12 | 13 |
| N-lauroyl valine n-butylamide | 3.0 | 19 |
| N-lauroyl sarcosine n-butylamide | 0.9 | 1.4 |
| N-palmitoyl-$\epsilon$-amino caproic acid n-butylamide | 3.0 | 4.0 |
| $N^\alpha, N^\epsilon$-dicapryloyllysine laurylamide | 153 | 89 |
| $N^\alpha, N^\epsilon$-dicapryloyllysine benzylamide | 12 | 13 |
| Laurylamine N-lauroyl valinate | 3.2 | 4.1 |
| Stearylamine N-lauroylalaninate | 3.1 | 4.2 |
| Laurylamine N-lauroylphenylalaninate | 4.0 | 74 |
| Stearlamine $N^\alpha, N^\epsilon$-dicapryloyllysinate | 17 | 61 |
| n-Butylamine $N^\alpha, N^\epsilon$-dilauroyllysinate | 20 | 25 |
| $N^\alpha, N^\epsilon$-dicapryloylornithine di-n-butyl amide | 1.9 | 2.9 |

In addition to the gelled kerosines in the table above, gelled kerosines having a shear strength more than 15 $g/cm^2$ were obtained using the following acid derivatives.

$N^\alpha, N^\delta$-dicaproyl-, $N^\alpha, N^\delta$-dilauroyl-, $N^\alpha, N^\delta$-dicocoylornithine; $N^\alpha, N^\delta$-dicaproyl-, $N^\alpha$,$N^\epsilon$-dicapryloyl-, $N^\alpha$,$N^\epsilon$-dilauroyl-, $N^\alpha$,$N^\epsilon$-dicocoyllysine; $N^\alpha$,$N^\delta$-dicapryloyl ornithine n-octyl, 2-ethylhexyl, decyl esters; $N^\alpha$,$N^\delta$-dilauroylornithine n-hexyl, n-octyl, 2-ethylhexyl, decyl, lauryl esters; $N^\alpha$,$N^\delta$-dicocoylornithine n-hexyl, n-octyl, 2-ethylhexyl, decyl, lauryl esters; $N^\alpha$,$N^\delta$-distearoylornithine n-hexyl, n-octyl, 2-ethylhexyl, decyl, lauryl ester; $N^\alpha$,$N^\delta$-ditallowylornithine n-hexyl, n-octyl, 2-ethylhexyl, decyl, lauryl ester;$N^\alpha$,$N^\delta$-dicapryloyllysine n-hexyl, n-octyl, 2-ethylhexyl, decyl esters; $N^\alpha$,$N^\delta$-dilauroyllysine n-hexyl, n-octyl, laruyl, 2-ethylhexyl, decylesters;$N^\alpha$,$N^\delta$-dicocoyllysine n-hexyl, n-octyl, lauryl, 2-ethylhexyl, decyl esters; $N^\alpha$,$N^\epsilon$-distearoyllysine n-octyl, lauryl, n-ethylhexyl, decyl esters; $N^\alpha$,$N^\epsilon$ ditallowyllysine n-hexyl, n-octyl, lauryl, 2-ethylhexyl, decyl esters; N-acetylglutamic acid-$\alpha$,$\gamma$-distearylamide; N-capryloylglutamic acid-$\alpha$,$\gamma$-diamide, di-n-butyl, di-isobutyl, di-n-octyl, di-2-ethylhexyl, dilauryl, distearylamide; N-cocoylglutamic acid-$\alpha$,$\gamma$-diamide, di-n-butyl, diisobutyl, di-n-octyl, di-2-ethylhexyl, dilauryl, distearylamide; N-stearoylglutamic acid-$\alpha$,$\gamma$-diamide, di-n-butyl, diisobutyl, di-n-octyl, di-2-ethylhexyl, dilauryl, distearylamide; N-tallowylglutamic acid-$\alpha$,$\gamma$-diamide, di-n-butyl, diisobutyl, di-n-octyl, di-2-ethylhexyl, dilauryl, distearylamide; N-lauroylglutamic acid-$\alpha$, $\gamma$-diisobutyl, dilaurylamide; $N^\alpha$,$N^\epsilon$-diacetyllysine lauryl, stearylamide; $N^\alpha$,$N^\epsilon$-dicapryloyllysine amide, n-butyl, isobutyl, n-octyl, 2-ethylhexyl, stearylamide; $N^\alpha$,$N^\epsilon$-dilauroyllysine amide, n-butyl, isobutyl, n-octyl, 2-ethylhexyl, lauryl, stearyl amide; $N^\alpha$,$N^\epsilon$-dicocoyllysine amide, n-butyl, isobutyl, n-octyl, 2-ethylhexyl, lauryl, stearylamide; $N^\alpha$,$N^\epsilon$-distearoyllysine amide, n-butyl, isobutyl, n-octyl, 2-ethylhexyl, lauryl, stearylamide; $N^\alpha$,$N^\epsilon$-ditallowyllysine amide, n-butyl, isobutyl, n-octyl, 2-ethylhexyl, lauryl, stearylamide; $N^\alpha$,$N^\epsilon$-dicapryloyllysine n-octyl-, 2-ethylhexyl-, lauryl-amine salt; $N^\alpha$,$N^\epsilon$-dilauroyllysine n-octyl-, 2-ethylhexyl-, lauryl-stearyl amine salt; $N^\alpha$,$N^\epsilon$-dicocoyllysine n-butyl-, isobutyl-, n-octyl-, 2-ethylhexyl-, lauryl-, stearyl amine salt; $N^\alpha$,$N^\epsilon$-distearoyllysine n-butyl-, isobutyl-, n-octyl-, 2-ethylhexyl-, lauryl-, stearyl amine salt; N,$N^\epsilon$-ditallowyllysine n-butyl, isobutyl-, n-octyl-, 2-ethylhexyl-, lauryl-, stearyl amine salt; $N^\alpha$,$N^\delta$-dicapryloylornithine n-octyl-, 2-ethylhexyl-, lauryl-, stearyl amine salt; $N^\alpha$,$N^\delta$-dilauroylornithine n-butyl-, isobutyl-, n-octyl-, 2-ethylhexyl-, lauryl-, stearyl amine salt $N^\alpha$,$N^\delta$-dicocoylornithine n-butyl-, isobutyl-, n-octyl-, 2-ethylhexyl-, lauryl-, stearyl amine salt; $N^\alpha$,$N^\delta$-distearoylornithine n-butyl-, isobutyl-, n-octyl-, 2-ethylhexyl-, lauryl, stearyl amine salt; $N^\alpha$,$N^\delta$-ditallowylornithine n-butyl-, isobutyl-, n-octyl-, 2-ethylhexyl-, lauryl-, stearyl amine salt.

EXAMPLE 2

Gelled non-polar organic liquids containing 1 wt% of $N^\alpha$,$N^\delta$-dicapryloylornithine, N-lauroylglutamic acid-$\alpha$, $\gamma$-di-n-butylamide or stearylamine $N^\alpha$,$N^\epsilon$-dilauroyllysinate were prepared by the procedure of Example 1 with the exception that the amino acid derivatives were dissolved in the nonpolar organic liquids at a temperature of 75° – 120°C. The results are tabulated below.

| Non-polar organic liquid | Shear Strength of Gel | | |
|---|---|---|---|
| | $N^\alpha$,$N^\delta$-dicapryloylornithine (g/cm²) | N-lauroylglutamic acid-$\alpha$-$\gamma$-di-n-butylamide (g/cm²) | Stearylamine $N^\alpha$,$N^\epsilon$-dilauroyllysinate (g/cm²) |
| Benzene | 30 | 131 | 12 |
| Cyclohexane | 14 | 75 | 18 |
| Heavy Oil *1 | 11 | 202 | 19 |
| Spindle Oil *2 | 17 | 345 | 30 |
| Turbine Oil *3 | 21 | 177 | 32 |
| Carbon tetrachloride | 102 | 10 | 12 |
| Dioctyl sebacate | 25 | 264 | 45 |
| n-Butyl acetate | 11 | 13 | 12 |
| Dioctyl phthalate | 15 | 87 | 33 |
| Methyl isobutyl ketone | 2.5 | 26 | 3.8 |
| Liquid paraffin | 16 | 398 | 57 |
| Polyoxypropylene *4 glycol monobutyl ether | 22 | 173 | 80 |
| Polyoxyethylene *5 glycol monooleate | 23 | 168 | 75 |
| Corn oil | 10 | 125 | 89 |
| Rapeseed oil | 12 | 189 | 108 |
| Soybean oil | 13 | 353 | 122 |
| Tricresyl phosphate | 2.1 | 217 | 15 |
| Gasoline | 12 | 162 | 16 |
| Gas oil | 15 | 211 | 19 |
| Xylene | 24 | 85 | 13 |
| Toluene | 16 | 62 | 9 |
| Cotton seed oil | 11 | 174 | 103 |
| Diisobutylketone | 3.0 | 35 | 4.5 |
| Diethyl phthalate | 15 | 83 | 28 |
| Octane | 8.0 | 63 | 15 |

*1 Viscosity of 2.1 C.P. (50°C)
*2 Viscosity of 4.0 cst (50° C) and a pour point below −5°C
*3 Viscosity of 17.5–22.5 cst (50°C) and a pour point below −5°C
*4 Containing 40 oxypropylene units
*5 Containing 5 oxyethylene units

EXAMPLE 3

A series of gelled kerosine samples containing from 0.1 to 5 wt% of N-lauroylglutamic acid-$\alpha$,$\gamma$-di-n-octylamide was prepared in the manner described in Example 1. The results are tabulated below.

| N-laurylglutamic acid-$\alpha,\gamma$-di-n-octylamide (wt%) | Shear strength of kerosine gel (g/cm$^2$) |
|---|---|
| 0.1 | 6 |
| 0.5 | 56 |
| 1.0 | 130 |
| 2.0 | 387 |
| 5.0 | 475 |

EXAMPLE 4

Three grams each of the powdered derivatives of the N-acylamino acids shown in the table below were admixed in 100 grams of a non-polar organic liquid. Each mixture was vigorously shaken for 10 minutes and allowed to stand overnight. Each mixture gelled and the results are tabulated below.

| Derivative of N-acylamino acid | Non-polar organic liquid | Shear strength of gel (g/cm$^2$) |
|---|---|---|
| $N^\alpha$,$N^\delta$-dicapryloylornithine | Benzene | 45 |
| " | Carbon tetrachloride | 140 |
| " | Kerosine | 23 |
| N-lauroylglutamic acid-$\alpha,\gamma$-di-n-octylamide | Benzene | 85 |
| N-lauroylglutamic acid-$\alpha,\gamma$-di-n-stearylamide | Benzene | 4.5 |

EXAMPLE 5

A series of experiments were conducted using N-lauroyl-glutamic acid-$\alpha,\gamma$-di-n-butylamide. One gram of N-lauroyl-glutamic acid-$\alpha,\gamma$-di-n-butylamide was dissolved in 5 ml of stirred ethyl acetate at a temperature of 60°C. The solution obtained was added to 100 grams of the stirred non-polar organic liquid. After standing for one hour, each solution gelled. The results are tabulated below.

| Non-polar organic liquid | Shear strength of gel (g/cm$^2$) |
|---|---|
| Ligroin | 89 |
| Kerosine | 185 |
| Gasoline | 83 |
| Heavy Oil | 145 |
| Liquid paraffin | 298 |
| Olive Oil | 176 |
| Soybean Oil | 212 |
| Rapeseed Oil | 153 |
| Corn Oil | 97 |

EXAMPLE 6

Gels of non-polar organic liquids were prepared containing 1 wt% of $N^\alpha$,$N^\epsilon$-dicapryloyllysine laurylester in the manner described in Example 5. The results are tabulated below.

| Non-polar organic liquid | Shear strength of gel (g/cm$^2$) |
|---|---|
| Kerosine | 18 |
| Cyclohexane | 13 |
| Heavy Oil | 25 |
| Liquid paraffin | 31 |
| Dioctyl phthalate | 16 |
| Polyoxypropyleneglycol monobutylether *1 | 52 |
| Olive Oil | 59 |

*1 Contains 40 oxypropylene units

EXAMPLE 7

A series of experiments were conducted using N-lauroylglutamic acid. Four grams of N-lauroylglutamic acid were dissolved in 10 ml of acetone at a temperature of 55°C. The solution was added to 100 grams of a stirred non-polar organic liquid. After standing overnight, the mixture gelled, and the results are tabulated below.

| Non-polar organic liquid | Shear strength of gel (g/cm$^2$) |
|---|---|
| Benzene | 3.0 |
| Spindle Oil | 4.5 |
| Olive Oil | 3.8 |

EXAMPLE 8

A series of experiments were conducted using N-lauroylalanine in the same manner as in Example 7. The results are tabulated below.

| Non-polar organic liquid | Shear strength of gel (g/cm$^2$) |
|---|---|
| Kerosine | 28 |
| Heavy Oil | 17 |
| Spindle Oil | 29 |
| Turbine Oil | 32 |

EXAMPLE 9

One gram each of the derivatives of the N-acylamino acids shown in the table below was admixed in 90 grams of a non-polar organic liquid, and each mixture was heated at a temperature of 80°C for 10 minutes. To each solution, 10 grams of water were added and each solution was vigorously shaken at a temperature of 80°C. After cooling to room temperature, each suspension had gelled. The results are tabulated below.

| Derivative of N-acylamino acid | Non-polar organic liquid | Shear Strength of gel (g/cm$^2$) |
|---|---|---|
| N-lauroylglutamic acid-$\alpha,\gamma$-distearylamide | Kerosine | 15 |
| " | Heavy Oil | 21 |
| " | Liquid Paraffin | 109 |
| " | Polyoxypropylene glycol mono-butyl ether *1 | 20 |
| " | Olive Oil | 91 |

-continued

| Derivative of N-acylamino acid | Non-polar organic liquid | Shear Strength of gel (g/cm$^2$) |
|---|---|---|
| N-lauroylvaline laurylamide | Liquid Paraffin | 3.5 |
| N$^\alpha$,N$^\epsilon$-dicapryloyllysine lauryl ester | " | 15 |
| Stearylamine N$^\alpha$,N$^\epsilon$-dicaproyl lysinate | Polyoxypropylene glycol mono-butyl ether *1 | 31 |
| N-capryloylleucine laurylamide | Liquid paraffin | 8.3 |
| Laurylamine N-lauroylphenyl-alaninate | Olive Oil | 62 |

*1 Contains 40 oxypropylene units

EXAMPLE 10

One gram of N-lauroylglutamic acid-α,γ-di-n-butylamide was dissolved in 5 ml of methanol at a temperature of 50°C. The solution was added slowly to the mixture of 70 grams of olive oil and 30 grams of water with vigorous stirring. After standing for 20 minutes, the mixture had gelled. The shear strength of the gel was 189 g/cm$^2$.

EXAMPLE 11

One-half gram of N-lauroylglutamic acid- α,γ-di-n-octylamide was dissolved in 5 ml of benzene at a temperature of 50°C. This solution was added to 1 liter of sea water having suspended therein 25 grams of heavy oil, and was stirred for 30 seconds. After standing for 20 minutes, the heavy oil solidified and floated on the surface of the sea water. The mixture was filtered through wire gauze (20 mesh) and 31 grams of solidified heavy oil was collected which contained benzene and a small amount of water. The content of the heavy oil in the mother liquor was below 75 ppm, as determined by measurements according to the procedure of Japanese Industrial Standards (JIS) K-0102. A similar experiment was conducted in which crude oil (Iranian heavy) was substituted for the heavy oil. Thirty grams of crude oil were collected and the content of the crude oil in the mother liquor was below 100 ppm.

EXAMPLE 12

One half ml or 0.1 ml of ethanol containing 10 wt/vol% of a derivative of an N-acylamino acid was added to 5 liters of water containing from 0.5 to 2.5 grams of a suspended non-polar organic liquid. The mixture was stirred vigorously for 10 minutes and then allowed to stand for 1 hour. The non-polar organic liquid solidified and floated. The solidified substance was removed by filtration. The residual amount of non-polar organic liquid in the mother liquor was measured by the methods of JIS K-0102 and the results are tabulated below.

| Derivative of N-acylamino acid | Admixed volume of ethanol solution (ml) | | Oil content | |
|---|---|---|---|---|
| | | | In the original water (ppm) | In the mother liquor (ppm) |
| N-lauroylglutamic acid-α,γ-di-n-butyl amide | 0.5 | Heavy Oil | 100 | 0.57 |
| N-caproylglutamic acid-α,γ-di-stearylamide | " | " | " | 0.71 |
| N-lauroyl valine laurylamide | " | " | " | 0.63 |
| N-palmitoylmethionine n-butyl amide | " | " | " | 3.95 |
| N-stearoylleucine benzyl amide | " | " | " | 3.55 |
| N-lauroylphenylalanine lauryl amide | " | " | " | 3.50 |
| N-capryloylglycine stearyl amide | " | " | " | 4.36 |
| N-stearoylserine 2-ethyl hexylamide | " | " | " | 5.93 |
| N$^\alpha$,N$^\epsilon$-dicapryloyl lysine lauryl ester | " | " | " | 0.59 |
| N-lauroyl-ε-amino caproic acid lauryl amide | " | " | " | 3.83 |
| Stearylamine N$^\alpha$,N$^\epsilon$-dicapryloyllysinate | " | " | " | 0.90 |
| N-lauroylglutamic acid-α,γ-di-n-butyl amide | " | Soybean Oil | " | 0.36 |
| " | " | Turbine Oil | " | 0.42 |
| N-lauroylglutamic acid-α,γ-di-stearylamide | 0.1 | Heavy Oil | " | 3.1 |
| " | 0.5 | " | 500 | 2.9 |
| " | 0.1 | Soybean Oil | 100 | 2.6 |
| " | 0.5 | " | 500 | 3.9 |

EXAMPLE 13

A series of experiments were conducted in the same manner described in Example 12 using water in which the non-polar organic liquid was emulsified with surfactants. The results are tabulated below.

|  | Admixed volume of ethanol solution (ml) | Oil and surfactant content | |
|---|---|---|---|
|  |  | In the original water (ppm) | In the mother liquor (ppm) |
| N-lauroylglutamic acid-ε,γ-di-n-butyl amide | 0.5 | Soybean Oil | 100 | 1.5 |
|  |  | Sodium dodecylsulfate (SDS) | 100 |  |
| " | " | Heavy Oil | 100 | 3.8 |
|  |  | SDS | 100 |  |
| N-lauroylglutamic acid-α,γ-di-stearylamide | " | " | 100 | 2.5 |
|  | " |  | 100 |  |
| " | " | Turbine oil | 100 | 2.1 |
|  |  | SDS | 100 |  |

EXAMPLE 14 (Cosmetics)

One gram of N-lauroylglutamic acid-α, γ-di-n-butylamide was dissolved in 45 grams of stirred liquid paraffin at a temperature of 120°C. To the stirred solution, 48.8 grams of olive oil, 5 grams of white vaseline, 0.2 grams of rose essence and a very small quantity of coloring matter were added at a temperature of 80°C. The resulting solution was cooled to room temperature. After standing for one hour, a gelled and clear hair conditioner was prepared.

EXAMPLE 15 (Cosmetics)

One gram of $N^\alpha$, $N^\epsilon$ -dicapryloyl lysine lauryl ester was dissolved at a temperature of 90°C in 68.8 grams of a solution which consisted of 54.1 grams of liquid paraffin, 4 grams of squalene, 4 grams of isopropylmyristate, 2 grams of bees wax, 4.5 grams of polyoxyethylene stearyl ether and 0.2 grams of methyl benzoate. To the solution, 27 grams of water and 3 grams of polyethylene glycol were added and the obtained suspension was shaken vigorously and an emulsion was formed at a temperature of 80°C. Then, the emulsion was cooled to a temperature of 60°C and 0.3 grams of rose essence were added thereto with stirring. The resulting emulsion was cooled to room temperature and allowed to stand overnight and then gelled. The gel obtained was a cleansing-jelly which spread well and adapted well on the skin.

EXAMPLE 16 (Paint)

Forty-five grams of chlorinated rubber (20% solution in toluene; viscosity of 10 centipoise), 18 grams of chlorinated paraffin, 58 grams of titanium dioxide, 70 grams of toluene, 4 grams of xylene and 4 grams of butyl acetate were mixed sufficiently in a ball mill. To the paint, 6 grams of a hot toluene solution containing 1 gram of N-lauroylglutamic acid-α,γ-di-n-butylamide was added with stirring. The solution was allowed to stand overnight, and the mixture gelled. The thixotropic properties of the paint (1) and a similar paint (2) containing no N-lauroylglutamic acid-α,γ-di-n-butylamide as a control were measured with a viscosimeter type B. The results are tabulated below.

| (A) | Viscosity at 6 rpm (cp) | (B) | Viscosity at 60 rpm (cp) | Ratio A/B |
|---|---|---|---|---|
| (1) | 8400 |  | 2400 | 3.5 |
| (2) | 550 |  | 540 | 1.0 |

Having now fully described this invention, it will be apparent to one of ordinary skill in the art that many changes and modifications can be made thereto without departing from the spirit or scope of the invention as set forth herein.

What is claimed as new and intended to be covered by letters patent is:

1. A process for preparing a gel, which comprises: homogeneously admixing a non-polar organic liquid having a dielectric constant of less than about 20 and having a solubility less than 10% by weight in water with an effective gel forming amount of at least one compound containing an N-acylamino acid component having the formula:

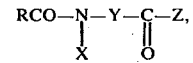

wherein RCO is a $C_2$ to $C_{30}$ aliphatic acyl group or an aralkylacyl group; Z is selected from the group consisting of hydroxy, $-NH_2$, $-OR_1$, $-NHR_2$,

and $-O-R_5NH_3^+$ wherein $R_1$, $R_2$, $R_3$, $R_4$ and $R_5$ are selected from the group consisting of $C_1$ to $C_{30}$ aliphatic hydrocarbon groups and aralkyl groups; X is selected from the group consisting of hydrogen and methyl; and Y is selected from the group consisting of

wherein $R_6$ is $C_1$ to $C_4$ alkyl, benzyl, phenyl, $-CH_2OH$,

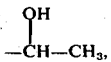

$-CH_2SH$, $-CH_2CH_2-S-CH_3$ or $-(CH_2)_p-COZ$ and p is a positive integer of 1 or 2 and Z is the same as above, $-(CH_2)_m NHCOR$, wherein m is a positive integer of 3 or 4 and COR is the same as above and $-(CH_2)_n-$, wherein n is a positive integer of 1 to 6; with the proviso that when Z is $-OR_1$,

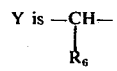

where $R_6$ is $-(CH_2)_m NHCOR$ and that at least one of R, $R_1$, $R_2$, $R_3$, $R_4$ and $R_5$ is a $C_5$ to $C_{30}$ aliphatic hydrocarbon group; and allowing the mixture to stand until gel formation occurs.

2. The process of claim 1, wherein said homogeneous admixing is conducted at temperatures ranging from room temperature up to the boiling point of said non-polar organic liquid.

3. The process of claim 1, wherein said compound containing an N-acylamino acid component is admixed with said non-polar organic liquid in the form of very fine powdered particles or as a solution.

4. The process of claim 1, wherein the effective gel forming amount of said compound containing an N-acylamino acid component added to said non-polar organic liquid is 0.05% to 20% by weight.

5. A process for preparing a gel, which comprises:
mixing a non-polar organic liquid having a dielectric constant of less than about 20 and having a solubility less than 10% by weight in water with 0.05 – 20% by weight based on said non-polar organic liquid of a compound containing an N-acylamino acid component having the formula (I),

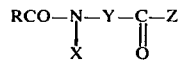

wherein RCO is a $C_2$ to $C_{30}$ aliphatic acyl group or an aralkyl acyl group; Z is selected from the group consisting of hydroxy, $-NH_2$, $-OR_1$, $-NHR_2$,

and $-O^-R_5NH_3^+$, wherein $R_1$, $R_2$, $R_3$, $R_4$ and $R_5$ are selected from the group consisting of $C_1$ to $C_{30}$ aliphatic hydrocarbon radicals and aralkyl radicals; X is selected from the group consisting of hydrogen and methyl; Y is selected from the group consisting of

wherein $R_6$ is $C_1$ to $C_4$ alkyl, benzyl, phenyl, $-CH_2OH$,

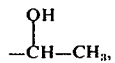

$-CH_2SH$, $-CH_2CH_2-S-CH_3$ or $-(CH_2)_p-COZ$ and p is a positive integer of 1 or 2 and Z is the same as above, $-(CH_2)_mNHCOR$, wherein m is a positive integer of 3 or 4 and COR is the same as above, and $-(CH_2)_n-$, wherein n is a positive integer of 1 to 6, with the proviso that when Z is $-OR_1$,

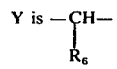

wherein $R_6$ is $-(CH_2)_mNHCOR$ and that at least one of R, $R_1$, $R_2$, $R_3$, $R_4$ and $R_5$ is a $C_6$ to $C_{30}$ aliphatic hydrocarbon group;
heating the mixture to effect solution;
cooling the resulting solution to room temperature; and thereafter;
allowing said cooled solution to stand until gel formation occurs.

6. The process of claim 5, wherein said non-polar organic liquid is a liquid hydrocarbon.

7. The process of claim 6, wherein said liquid hydrocarbon is selected from the group consisting of gasoline, naphthas, kerosine, gas oil, heavy oil, crude oil, spindle oil, turbine oil, liquid paraffin, benzene, oxlene, toluene, hexane, heptane, octane and cyclohexane.

8. The process of claim 5, wherein said non-polar organic liquid is a fatty oil.

9. The process of claim 8, wherein said fatty oil is selected from the group consisting of corn oil, soybean oil, olive oil, rape seed oil and cotton seed oil.

10. The process of claim 5, wherein said non-polar organic liquid is an ester.

11. The process of claim 10, wherein said ester is selected from the group consisting of butyl acetate, diethyl phthalate, dioctyl phthalate, dioctyl sebacate and tricresyl phosphate.

12. The process of claim 5, wherein said non-polar organic liquid is a ketone selected from the group consisting of methyl isobutyl ketone and diisobutyl ketone.

13. The process of claim 5, wherein said non-polar organic liquid is a normally liquid polyoxyalkylene monoalkyl ether.

14. The process of claim 13, wherein said polyoxyalkylene monoalkyl ether is polyoxyethylene monolauryl ether containing 4 to 6 oxyethylene units or polyoxypropylene monoalkyl ethers wherein the alkyl group has 4 to 12 carbon atoms and the number of oxypropylene units is 10 to 50.

15. The process of claim 5, wherein said non-polar organic liquid is a normally liquid polyoxyalkylene glycol fatty acid ester.

16. The process of claim 15, wherein said polyoxyalkylene glycol fatty acid ester is polyoxyethylene lauric or oleic acid ester containing 4 to 6 oxyethylene units.

17. A process for preparing a gel, which comprises:
homogeneously admixing a non-polar organic liquid having a dielectric constant of less than about 20 and having a solubility less than 10% by weight in water with 0.05% to 20% by weight of at least one compound containing an N-acylamino acid component having the formula

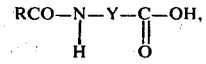

wherein RCO is a $C_5$ to $C_{30}$ aliphatic acyl, and Y is selected from the group consisting of

wherein $R_6$ is a $C_1$ to $C_4$ alkyl and $-(CH_2)_mNHCOR$, wherein m is a positive integer of 3 or 4 and COR is the same as above; and
allowing the mixture to stand until gel formation occurs.

18. The process of claim 17, wherein said compound containing an N-acylamino acid component is selected from the group consisting of N-lauroylalanine, $N^\alpha$, $N^\delta$-dicaproyl ornithine, $N^\alpha$, $N^\delta$-dicapryloyl orinthine, $N^\alpha$, $N^\delta$-dilauroylornithine, $N^\alpha$, $N^\epsilon$ - dicocoylornithine, $N^\alpha, N^\epsilon$-dicaproyllysine and $N^\alpha, N^\epsilon$-dicapryloyllysine.

19. A process for preparing a gel, which comprises: homogeneously admixing a non-polar organic liquid having a dielectric constant of less than 20 and having a solubility less than 10% by weight in water with 0.05% to 20% by weight of a compound containing N-acylamino acid component having the formula

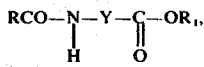

wherein RCO is a $C_2$ to $C_{30}$ aliphatic acyl group or an aralkylacyl group; $R_1$ is a $C_1$ to $C_{30}$ aliphatic hydrocarbon group or an aralkyl; and

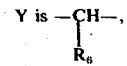

wherein $R_6$ is $-(CH_2)_m NHCOR$, $m$ is a positive integer of 3 or 4 and RCO is the same as above, with the proviso that at least one of R and $R_1$ is a $C_5$ to $C_{30}$ aliphatic hydrocarbon group; and allowing the mixture to stand until gel formation occurs.

20. The process of claim 19, wherein said compound containing an N-acylamino acid component is an $N^\alpha, N^\delta$-dicapryloylornithine alkyl ester, wherein said alkyl group has 6 to 18 carbon atoms; $N^\alpha, N^\delta$-dilauroylornithine alkyl ester, wherein said alkyl group has 6 to 18 carbon atoms; $N^\alpha, N^\delta$-dicocoylornithine alkyl ester, wherein said alkyl group has 6 to 18 carbon atoms; $N^\alpha, N^\delta$-distearoylornithine alkyl ester, wherein said alkyl group has 6 to 18 carbon atoms; $N^\alpha, N^\delta$-ditallowylornithinealkyl ester, wherein said alkyl group has 6 to 18 carbon atoms; $N^\alpha, N^\epsilon$-dicapryloyllysine alkyl ester, wherein said alkyl group has 6 to 18 carbon atoms; $N^\alpha, N^\epsilon$-dilauroyllysine alkyl ester, wherein said alkyl group has 6 to 18 carbon atoms; $N^\alpha, N^\epsilon$-dicocoyllysine alkyl ester, wherein said alkyl group has 6 to 18 carbon atoms; $N^\alpha, N^\epsilon$-distearoyllysine alkyl ester, wherein said alkyl group has 6 to 18 carbon atoms or $N^\alpha, N^\epsilon$-ditallowyllysine alkyl ester, wherein said alkyl group has 6 to 18 carbon atoms.

21. A process for preparing a gel, which comprises: homogeneously admixing a non-polar organic liquid having a dielectric constant of less than 20 and having a solubility less than 10% by weight in water with 0.05% to 20% by weight of a compound containing an N-acylamino acid component having the formula

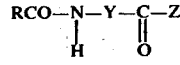

wherein RCO is a $C_2$ to $C_{30}$ aliphatic acyl group or an aralkyl acyl group; Z is $-NH_2$, $-NHR_2$ or

wherein $R_2$, $R_3$ and $R_4$ are selected from the group consisting of $C_1$ to $C_{30}$ aliphatic hydrocarbon groups and aralkyl groups; and

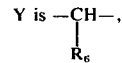

wherein $R_6$ is $C_1$ to $C_4$ alkyl, benzyl, $-CH_2CH_2-S-CH_3$, or $-(CH_2)_p$-COZ wherein $p$ is a positive integer of 1 or 2 and Z is the same as above; $-(CH_2)_m NHCOR$, wherein m is a positive integer of 3 or 4 and COR is the same as above and $-(CH_2)_n-$, wherein $n$ is a positive integer of 1 to 6, with the proviso that at least one of R, $R_2$, $R_3$, and $R_4$ is a $C_5$ to $C_{30}$ aliphatic hydrocarbon group; and allowing the mixture to stand until gel formation occurs.

22. The process of claim 21, wherein said compound containing an N-acylamino acid component is N-acetyl glutamic acid-α,γ-dialkyl amide, wherein said alkyl group has 12 to 18 carbon atoms; N-caproyloylglutamic acid-α,γ-diamide, N-caprylyl glutamic acid-α,γ-dialkylamide, wherein said alkyl group has 1 to 18 carbon atoms; N-lauroylglutamic acid-α,γ-diamide, N-lauroylglutamic acid-α,γ-dialkylamide, wherein said alkyl group has 1 to 18 carbon atoms; N-cocoylglutamic acid-α,γ-diamide, N-cocoylglutamic acid-α,γ-dialkylamide, wherein said alkyl group has 1 to 18 carbon atoms; N-stearoylglutamic acid-α,γ-diamide, N-stearoylglutamic acid-α,γ-dialkylamide, wherein said alkyl group has 1 to 18 carbon atoms; N-tallowylglutamic acid-α,γ-diamide, N-(tallowyl)glutamic acid-α,γ-dialkylamide, wherein said alkyl group has 1 to 18 carbon atoms; $N^\alpha, N^\epsilon$-diacetyllysine alkylamide, wherein said alkyl group has 12 to 18 carbon atoms; $N^\alpha, N^\epsilon$-dicapryloyllysine amide, $N^\alpha, N^\epsilon$-dicapryloyllysine alkylamide, wherein said alkyl group has 1 to 18 carbon atoms; $N^\alpha, N^\epsilon$-dilauroyllysine amide, $N^\alpha, N^\epsilon$-dilauroyllysine alkylamide, wherein said alkyl group has 1 to 18 carbon atoms; $N^\alpha, N^\epsilon$-dicocoyllysine amide, $N^\alpha, N^\epsilon$-dicocoyllysine alkylamide, wherein said alkyl group has 1 to 18 carbon atoms; $N^\alpha, N^\epsilon$-distearoyllysine amide, $N^\alpha, N^\epsilon$-distearoyllysine alkylamide, wherein said alkyl group has 1 to 18 carbon atoms; or $N^\alpha, N^\epsilon$-di(tallowyl)lysine amide, $N^\alpha, N^\epsilon$-di(tallowyl)lysine alkylamide, wherein said alkyl group has 1 to 18 carbon atoms.

23. A process for preparing a gel, which comprises: homogeneously admixing a non-polar organic liquid having a dielectric constant of less than 20 and having a solubility less than 10% by weight in water with 0.05% to 20% by weight of a compound containing an N-acylamino acid component having the formula

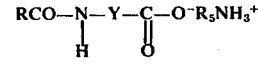

wherein RCO is a $C_2$ to $C_{30}$ aliphatic acyl group or an aralkyl acyl group; $R_5$ is a $C_1$ to $C_{30}$ aliphatic hydrocarbon group or an aralkyl; and Y

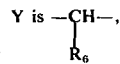

wherein $R_6$ is selected from the group consisting of $C_1$ to $C_4$ alkyl, benzyl or —$(CH_2)_m$NHCOR, and $m$ is a positive integer of 3 or 4 and COR is the same as above, with the proviso that at least one of R and $R_5$ is a $C_5$ to $C_{30}$ aliphatic hydrocarbon group; and allowing the mixture to stand until gel formation occurs.

24. The process of claim 23, wherein said compound containing an N-acylamino acid component is an $N^\alpha$,$N^\delta$-dicapryloyllysine alkylamine salt, wherein said alkylamine has 8 to 18 carbon atoms; an $N^\alpha$,$N^\epsilon$-dilauroyllysine alkylamine salt, wherein said alkylamine has 4 to 18 carbon atoms; an $N^\alpha$,$N^\epsilon$-dicocoyllysine alkylamine salt, wherein said alkylamine has 4 to 18 carbon atoms; an $N^\alpha$,$N^\epsilon$-distearoyllysine alkylamine salt, wherein said alkylamine has 4 to 18 carbon atoms; an $N^\alpha$,$N^\epsilon$-ditallowyllysine alkylamine salt, wherein said alkylamine has 4 to 18 carbon atoms; an $N^\alpha$,$N^\delta$-dicapryloylornithine alkylamine salt, wherein said alkylamine has 8 to 18 carbon atoms; an $N^\alpha$,$N^\delta$-dilauroylornithine alkylamine salt, wherein said alkylamine has 4 to 18 carbon atoms; an $N^\alpha$,$N^\delta$-dicocoylornithine alkylamine salt, wherein said alkylamine has 4 to 18 carbon atoms; an $N^\alpha$,$N^\delta$ distearoylornithine alkylamine salt, wherein said alkylamine has 4 to 18 carbon atoms; an $N^\alpha$,$N^\delta$-ditallowylornithine alkylamine salt, wherein said alkylamine has 4 to 18 carbon atoms; an N-lauroylphenylalanine alkylamine salt, wherein said alkylamine has 8 to 18 carbon atoms; an N-cocoylphenylalanine alkylamine salt, wherein said alkylamine has 8 to 18 carbon atoms; an N-stearoylphenylalanine alkylamine salt, wherein said alkylamine has 8 to 18 carbon atoms, or an N-tallowylphenylalanine alkylamine salt, wherein said alkylamine has 8 to 18 carbon atoms.

25. A gel, consisting essentially of:
a homogeneous mixture of a non-polar organic liquid having a dielectric constant of less than 20 and having a solubility less than 10% by weight in water and 0.05% to 20% by weight of at least one compound containing an N-acylamino acid component having the formula

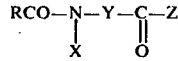

wherein RCO is a $C_2$ to $C_{30}$ aliphatic acyl group or an aralkyl acyl group; Z is hydroxy, —$NH_2$, —$OR_1$, —$NHR_2$,

or —$O^-R_5NH_3^+$, wherein $R_1$, $R_2$, $R_3$, $R_4$ and $R_5$ is a $C_2$ to $C_{30}$ aliphatic hydrocarbon group and aralkyl groups; X is hydrogen or methyl; and

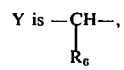

wherein $R_6$ is $C_1$ to $C_4$ alkyl, benzyl, phenyl, —$CH_2OH$,

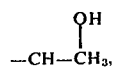

—$CH_2SH$, —$CH_2CH_2$—S—$CH_3$ or —$(CH_2)_p$COZ; and $p$ is a positive integer of 1 or 2, and Z is the same as above; —$(CH_2)_m$NHCOR, wherein $m$ is a positive integer of 3 or 4 and COR is the same as above, or —$(CH_2)_n$—, wherein $n$ is a positive integer of 1 to 6, with the proviso that when Z is —$OR_1$,

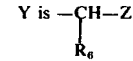

wherein $R_6$ is —$(CH_2)_m$NHCOR and that at least one of R, $R_1$, $R_2$, $R_3$, $R_4$ and $R_5$ is a $C_5$ to $C_{30}$ aliphatic hydrocarbon group.

26. The gel of claim 25, wherein said non-polar organic liquid is selected from the group consisting of gasoline, naphthas, kerosine, gas oil, heavy oil, crude oil, spindle oil, turbine oil, liquid paraffin, benzene, xylene, toluene, hexane, heptane, octane, cyclohexane, corn oil, soybean oil, olive oil, rapeseed oil, cotton seed oil, butyl acetate, diethyl phthalate, dioctyl phthalate, dioctyl sebacate, tricresyl phosphate, methyl isobutyl ketone, diisobutyl ketone, liquid polyoxyethylene, monolauryl ether, liquid polyoxyethylene monostearyl ether, liquid polyoxypropylene monobutyl ether, liquid polyoxypropylene monolauryl ether, liquid polyoxypropylene monostearyl ether, liquid polyoxyethylene glycol lauric acid ester, liquid polyoxypropylene glycol oleic acid ester and mixtures thereof.

27. A gel, consisting essentially of a homogeneous mixture of a non-polar organic liquid having a dielectric constant of less than 20 and having a solubility less than 10% by weight in water, and 0.05% – 20% by weight of at least one compound having the formula

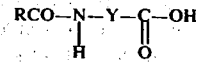

wherein RCO is $C_5$ to $C_{30}$ aliphatic acyl, and

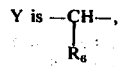

wherein $R_6$ is $C_1$ to $C_4$ alkyl or —$(CH_2)_m$NHCOR, wherein $m$ is a positive integer of 3 or 4 and COR is the same as above.

28. A gel, consisting essentially of:
a homogeneous mixture of a non-polar organic liquid having a dielectric constant of less than 20 and having a solubility less than 10% by weight in water and 0.05% to 20% by weight of at least one cmpound having the formula

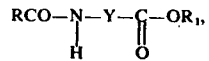

wherein RCO is a $C_2$ to $C_{30}$ aliphatic acyl group or an aralkyl acyl group; $R_1$ is a $C_1$ to $C_{30}$ aliphatic hydrocarbon group or an aralkyl group, and

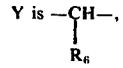

wherein $R_6$ is $-(CH_2)_m NHCOR$,
wherein $m$ is a positive integer of 3 or 4 and RCO is the same as above, with the proviso that at least one of R and $R_1$ is a $C_5$ to $C_{30}$ aliphatic hydrocarbon group.

29. A gel, consisting essentially of:
a homogeneous mixture of a non-polar organic liquid having a dielectric constant of less than 20 and having a solubility less than 10% by weight in water and 0.05% to 20% by weight of at least one compound having the formula

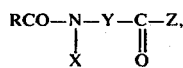

wherein RCO is a $C_2$ to $C_{30}$ aliphatic acyl group or an aralkyl acyl group; Z is $-NH_2$ or $-NHR_2$, wherein $R_2$ is a $C_1$ to $C_{30}$ aliphatic hydrocarbon group or aralkyl group; and

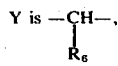

wherein $R_6$ is $C_1$ to $C_4$ alkyl, benzyl, $-CH_2CH_2-S-CH_3$ or $-(CH_2)_p-COZ$, wherein $p$ is a positive integer of 1 or 2 and Z is the same as above, or $-(CH_2)_m COR$, wherein $m$ is a positive integer of 3 or 4 and COR is the same as above, with the proviso that at least one of R and $R_2$ is a $C_5$ to $C_{30}$ aliphatic hydrocarbon group.

30. A gel, consisting essentially of:
a homogeneous mixture of a non-polar organic liquid having a dielectric constant of less than 20 and having a solubility less than 10% by weight in water, and 0.05% to 20% by weight of at least one compound having the formula

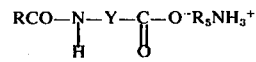

wherein RCO is $C_2$ to $C_{30}$ aliphatic acyl; $R_5$ is a $C_1$ to $C_{30}$ aliphatic hydrocarbon group or an aralkyl group; and Y is $C_1$ to $C_4$ alkyl, benzyl or $-(CH_2)_m NHCOR$, wherein $m$ is a positive integer of 3 or 4 and COR is the same as above, with the proviso that at least one of R and $R_5$ is a $C_5$ to $C_{30}$ aliphatic hydrocarbon group.

* * * * *